United States Patent [19]
Stolz et al.

[11] Patent Number: 5,235,625
[45] Date of Patent: Aug. 10, 1993

[54] METHOD FOR SYNCHRONIZING PARTICLE COUNTERS TO EXTERNAL EVENTS

[75] Inventors: James B. Stolz, Milpitas; Yung C. Lee, Cupertino; Peter G. Borden, San Mateo, all of Calif.

[73] Assignee: High Yield Technology, Sunnyvale, Calif.

[21] Appl. No.: 825,687

[22] Filed: Jan. 27, 1992

[51] Int. Cl.5 .............................................. G06M 7/00
[52] U.S. Cl. ........................................ 377/10; 377/12
[58] Field of Search .................................. 377/10, 12

[56] References Cited

U.S. PATENT DOCUMENTS

| | | |
|---|---|---|
| 4,550,417 | 10/1985 | Nunogaki et al. ............... 377/10 |
| 4,782,500 | 11/1988 | Lyngsie ............................ 377/10 |
| 4,837,705 | 6/1989 | Mussler et al. .................. 377/10 |

Primary Examiner—William L. Sikes
Assistant Examiner—Scott A. Ouellette
Attorney, Agent, or Firm—Skjerven, Morrill, MacPherson, Franklin & Friel

[57] ABSTRACT

A method and an apparatus for synchronizing particle counts to process events provide a trigger signal related to the process events in lieu of a time-based trigger signal. In one embodiment, the controller to a particle counter further subdivides a process event into subintervals to allow profiling of particle counts during the process event. In one embodiment, the controller of the particle counter receives multiple trigger signals corresponding to multiple trigger signal sources, each trigger signal source being identified by a source tag. Particle counts and time-stamps are maintained for each source of the trigger signals.

8 Claims, 1 Drawing Sheet

METHOD FOR SYNCHRONIZING PARTICLE COUNTERS TO EXTERNAL EVENTS

FIELD OF THE INVENTION

This invention relates to particle counters, and in particular to particle counters used in process control equipment.

BACKGROUND OF THE INVENTION

A particle counter accumulates the number of particles detected during a period of time. An application of a particle counter may be found in equipment of a manufacturing process which is sensitive to free particles, such as semiconductor manufacturing equipment.

Typically, a timer in the particle counter, or its controller, controls the beginning and end points of a count period. At the end of the count period, the particle count is displayed and stored. Thereafter, the particle counter is reset prior to particle counting in the next period. Such particle counter expresses the count in units of, for example, "counts per minute." Thus, the count period is a basic parameter of standard particle counting. However, when a particle counter is attached to a piece of process equipment which can be used in numerous process variations, simple time-based particle counting has a number of disadvantages.

For example, when the particle counter is used to control a process (e.g. in a "statistical process control" application), the number of particles per process event must be captured and analyzed. If the particle counter is not initially synchronized to process events, the resulting particle counts re accumulated over the duration of fixed time periods bearing little relation to the process events. Also, a process event may be of variable duration, so that the number of fixed intervals will vary. In that situation, a "particles-per-event" count is necessary for process control purposes. Thus, particle counts obtained using the prior art methods cannot be used at a later time to relate the particles detected to the process events within the process cycle.

To obtain finer resolution of particle counts when a number of process events are occurring over the count period, time-based particle counting over short time intervals generates too much data. Conversely, long count periods in these applications result in poor resolution. Further, because count periods are out of step with process events, it may be difficult to use the count data for an application such as isolating the process event which contributes most to the particle count.

In certain applications, it is desirable not only to determine which process event causes particle generation, but also whether the particles are generated at the beginning, at the intermediate, or at the end phases of a process event. Such information can often facilitate troubleshooting the process equipment for detecting the source of particle generation.

Another disadvantage of time-based particle counting results from running the particle counter regardless of whether significant process events are taking place inside the process equipment, thereby causing much useless data to be acquired and stored even during equipment dead time.

SUMMARY OF THE INVENTION

In accordance with the present invention, a method and an apparatus are provided in a particle counter to relate particle counts to process events. The method in accordance with the present invention provides a trigger signal having two states related to the process events. This trigger signal is provided to the controller of the particle counter to initiate and terminate count periods in accordance with the state of the trigger signal. Thus, both the initiation and the termination of the count period are related to the and termination signals which are timer-based.

In one embodiment, the count period is further subdivided into subintervals for particle counting during each sub-interval, so as to further count resolution within a process event. Time stamps indicating the beginning and the end of a count period are provided for each count period.

In one embodiment, the controller to the particle counter receives multiple trigger signals from various sources representing a plurality of process events. The controller maintains separate particle counts and time stamps for each source of trigger signal.

By relating particle counts to process events, the present invention provides particle count per process cycle statistics useful for statistical process control applications.

By providing multiple trigger signals each relating to a different process event, and by tailoring the duration of the count period of each process event, fine resolution for relating a particle count to its corresponding process event can be maintained.

By providing subintervals during the count period of a process event, particle count profiles can be assembled from particle counts at various phases of a process event to facilitate troubleshooting in the process equipment for the source of particle generation.

In addition, because durations of count periods are tailored to process events, only the necessary data are collected, thereby overcoming the disadvantage of too much or too little data in time-based particle count periods of the prior art.

The present invention is better understood upon consideration of the following detailed description and the accompanying drawings.

DETAILED DESCRIPTION OF THE PREFERRED EMBODIMENTS

Figure 1:
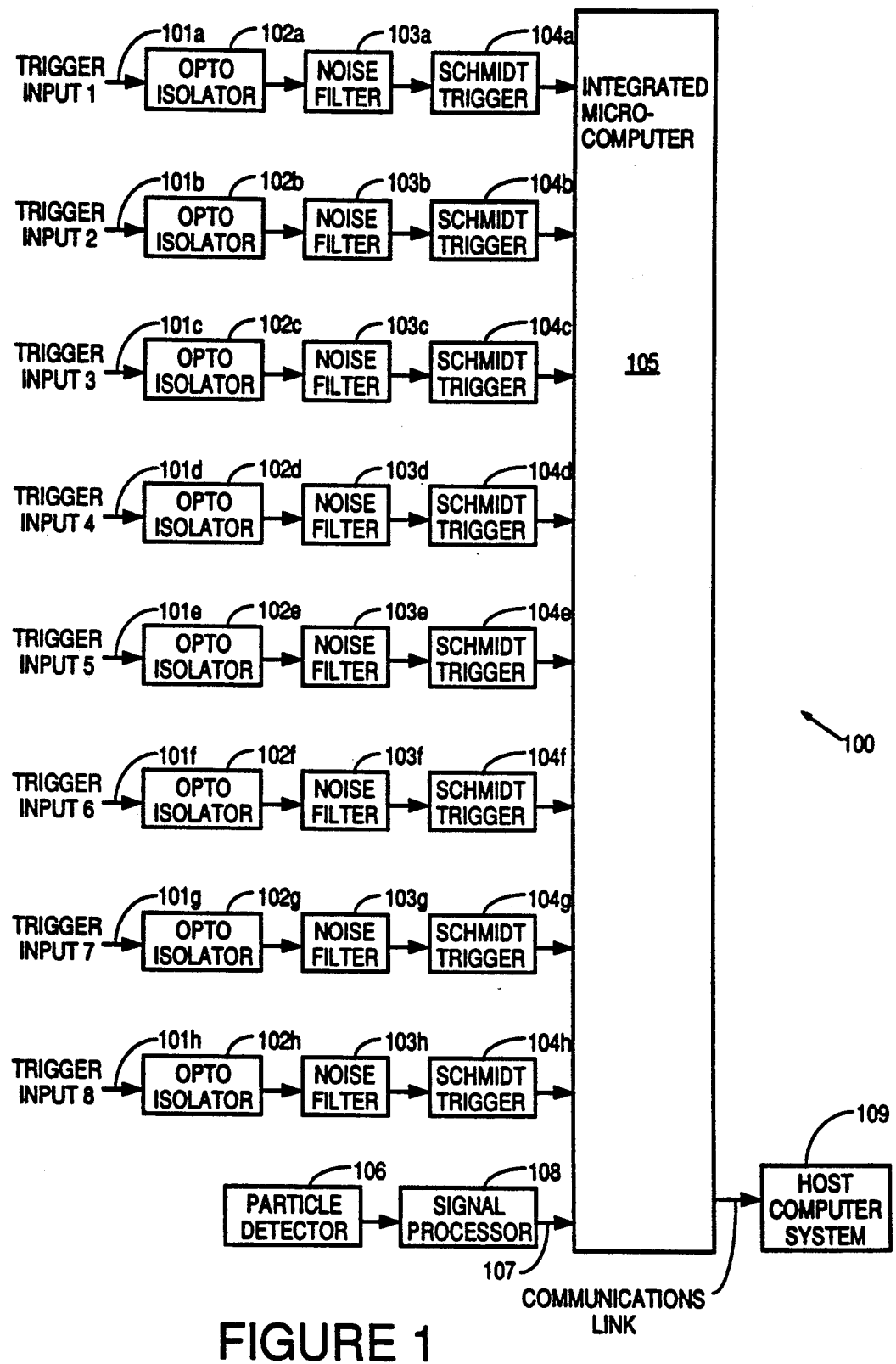
FIG. 1 is a block diagram of a machine trigger circuit 100 showing trigger signals received from a number of process equipment sources, in accordance with the present invention.

The present invention synchronizes particle counts with process events. A process event can be a wafer etching step, an ion implantation step involving a batch of wafers, or the pumping of a process chamber. One result of the present invention is the ability to express particle counts in units of "particles per process event", which are useful for statistical process control. Consequently, one can directly compare particle counts for each process cycle to those particle counts collected under control conditions.

An embodiment of the present invention supports particle counting by providing a machine trigger circuit which synchronizes particle counts with process events using one of a number of ways: (a) simple machine trigger, (b) start-stop machine trigger, (c) interval machine trigger, and (d) subcycle machine trigger.

In a simple machine trigger, a single signal is provided from the process equipment to the controller of the particle counter. This single signal is used to control both the beginning and the end of a particle count period. Such trigger signal is related to a process event occurring in the equipment. For example, in a plasma etcher, such trigger signal may be set to an active state when a plasma etchant is introduced, and set to an inactive state when an end point of etching is detected. When the trigger signal transitions to an active state, a particle count is initiated. However, when the signal transitions to an inactive state, particle count stops until the trigger signal's next transition to the active state.

In a start-stop machine trigger, however, the process equipment provides two pulses to the controller of the particle counter, such that when a first pulse is received, particle counting is initiated, and when a second pulse is received, particle counting is terminated. In the start-stop machine trigger operation, each pulse is associated with a simple process event. The pulses can be provided to the controller of the particle counter over a single trigger signal, or over separate trigger signals.

An interval machine trigger, in addition to providing control for initiating and terminating particle count as provided by either a simple machine trigger or a start-stop machine trigger, further provides a timer to divide a count period into a number of shorter sub-intervals. In this embodiment, with the exception of the last sub-interval, each sub-interval is a period of time having a programmable duration. In this manner, particle count profiles can be generated from the particle counts collected in the sub-intervals, so as to allow more detailed understanding of a process event. Interval machine trigger operation is useful in such application as determining which part of a process event accounts for generating most particles. The total count over the process event is obtained by summing the individual counts of the sub-intervals. Such total count can also be used for process control.

A sub-cycle trigger receives a number of trigger input signals, each of which may be provided by a different part of the process equipment. Under a sub-cycle trigger, each trigger input signal corresponds to a particular "state" of the equipment, and a particle count is separately stored for each of these states. For example, an etch process cycle may contain such subcycles as a pump-down subcycle, an etch subcycle and a "vent-to-air" subcycle. A sub-cycle trigger is particularly suited for relating particle counts to process events, e.g. when used to locate a particle source.

A block diagram of a machine trigger circuit 100 in the present embodiment is shown in FIG. 1. As shown in FIG. 1, up to eight trigger signals 101a-h are received from one or more pieces of process equipment. Each of trigger signals 101a-h is connected to a corresponding one of opto-isolators 102a-h in the present embodiment. Although eight opto-isolators are shown, there is no limit to the number of trigger input signals receivable by any embodiment of the present invention. Machine trigger input signals may originate from various sources, such as (a) a computer for controlling one or more pieces of process equipment; (b) a contact closure sensor which detects motion in equipment doors, or other moving apparatus; (c) a voltage across a valve; or (d) an internal timing signal of a piece of process equipment.

Opto-isolators 102a-h serve to eliminate undesirable ground loops, which may be possible when different equipment at different ground potentials are connected together at one machine trigger circuit, such as machine trigger circuit 100. Such connections are possible when the sources of trigger signals are process equipment located in different parts of a building. By using an opto-isolator, no electrical connection can be inadvertently made, since the on/off information is transmitted through an optical interface.

After being electrically decoupled from its source by one of opto-isolator 102a-h, a trigger signal then passes in succession through a noise filter (e.g. one of noise filters 103a-h) and a schmidt trigger (e.g. one of schmidt triggers 104a-h). Most process equipment are located in noisy environments, and the equipment themselves also generate much electrical noise. A noise filter smooths the trigger signal by eliminating noise spikes. A schmidt trigger then provides a rapid transition of the smoothed signal, so as to reconstruct a crisp signal corresponding to the original trigger signal. Hence, the signal provided by each of Schmidt triggers 104a-h is slightly delayed with respect to the original trigger it tracks. For most applications, this delay is not significant.

Each trigger signal emerging from Schmidt triggers 104a-h is received by a microprocessor 105, which also receives a particle count signal on lead 107 from particle detector 106. The particle count signal on lead 107 is provided after noise is eliminated by signal processing circuit 108. Microprocessor 105 communicates with a host system 109, which displays and analyzes particle counts received from microprocessor 105. Host system 109 may also be used to supervise the real-time operation of the process equipment.

During operation, when none of trigger signals 101a-h is active (i.e. no particle counting activity is desired), microprocessor 105 idles particle detector 106. However, when any of trigger signals 101a-h becomes active, microprocessor 105 initiates particle detector 106 for particle counting, and records both the start time and the "source tag", which indicates the source of trigger signal ("channel"). If microprocessor 105 is set to interval machine trigger mode of operation, microprocessor 105 records the particle count at the end of each sub-interval count period with a time stamp. At the end of each sub-interval count period, particle detector 106 is reset to zero and particle counting is initiated at the beginning of the next sub-interval count period. Particle count continues until the trigger signal become inactive. At that time, particle detector 106 is idled, and the particle count for the last sub-interval count period is recorded and time stamped.

The counts and time-stamps recorded are available for the host system to display and further analyze. Should a trigger signal become active while another trigger signal is in active state, microprocessor 105 initiates a second channel of data similar to that created for the first channel. Separate sub-interval count periods and time-stamps are maintained in each channel. Microprocessor 105 maintains in a memory buffer by source tags the particle counts and the time stamps recorded. The memory buffer is available for access by host computer 109.

The above detailed description is provided to illustrate the specific embodiments of the present invention and is not intended to be limiting. Numerous modifications and variations within the scope of the present invention are possible. The present invention is defined by the following claims.

We claim:

1. A method, in a particle counter, for synchronizing a particle count to a process event in a manufacturing process, comprising the steps of:

coupling said particle counter to a process equipment so as to receive in said particle counter a first trigger signal having active and inactive states, said process equipment setting said active and inactive states of said first trigger signal to indicate respectively a beginning point and an ending point of said process event; and providing a controller, receiving said first trigger signal, for initiating and terminating a particle count period in said particle counter, in response to said active and inactive states of said first trigger signal.

2. A method as in claim 1, wherein said step of providing a controller to said particle counter provides a controller receiving a plurality of trigger signals, each of said plurality of trigger signals having active and inactive states as in said first trigger signal, said controller maintaining separate particle count periods for each of said plurality of trigger signals.

3. A method for synchronizing a particle count to process events in a particle counter, comprising the steps of:

providing a first trigger signal having active and inactive states, each state being related to an occurrence of said process events;

providing a controller for initiating and terminating particle count periods in said particle counter, said controller receiving said first trigger signal; and initiating a particle count period when said first trigger signal is active and terminating said particle count period when said trigger signal is inactive;

wherein said step of initiating said particle counter further comprises the steps of:

dividing said particle count period into sub-intervals; and recording a particle count and a time stamp for each subinterval.

4. A method for synchronizing a particle count to process events in a particle counter, comprising the steps of:

providing a first trigger signal having active and inactive states, each state being related to an occurrence of said process events;

providing a controller for initiating and terminating particle count periods in said particle counter, said controller receiving said first trigger signal; and initiating a particle count period when said first trigger signal is active and terminating said particle count period when said trigger signal is inactive;

wherein said step of initiating said count period records a first time stamp when said count period is initiated and provides a second timestamp when said count period is terminated.

5. An apparatus for synchronizing a particle count to a process event in a particle counter, comprising:

an interface between said particle counter and a process equipment for receiving a first trigger signal having active and inactive states, said process equipment setting said active and inactive states of said first trigger signal to indicate respectively a beginning point and an ending point of said process event;

a controller, receiving said first trigger signal from said interface, for initiating and terminating particle count periods in said particle counter, in response to said active and inactive states of said first trigger signal.

6. An apparatus as in claim 5, wherein said controller to said particle counter receives a plurality of trigger signals, each of said plurality of trigger signals having active and inactive states as in said first trigger signal, said controller maintaining separate particle count periods for each of said plurality of trigger signals.

7. An apparatus for synchronizing a particle count to process events in a particle counter, comprising:

means for providing a first trigger signal having active and inactive states, each state being related to an occurrence of said process events;

a controller for initiating and terminating particle count periods in said particle counter, said controller receiving said first trigger signal; and means for initiating a particle count period when said first trigger signal is active and terminating said particle count period when said trigger signal is inactive; wherein said means for initiating said particle counter further comprises:

means for dividing said particle count period into sub-intervals; and means for recording a particle count and a time stamp for each subinterval.

8. An apparatus for synchronizing a particle count to process events in a particle counter, comprising:

means for providing a first trigger signal having active and inactive states, each state being related to an occurrence of said process events;

a controller for initiating and terminating particle count periods in said particle counter, said controller receiving said first trigger signal; and means for initiating a particle count period when said first trigger signal is active and terminating said particle count period when said trigger signal is inactive;

wherein said means for initiating said count period records a first timestamp when said count period is initiated and provides a second timestamp when said count period is terminated.

* * * * *

UNITED STATES PATENT AND TRADEMARK OFFICE
CERTIFICATE OF CORRECTION

PATENT NO.    : 5,235,625
DATED         : August 10, 1993
INVENTOR(S)   : James B. Stolz, Yung C. Lee and Peter G. Borden It is certified that error appears in the above-identified patent and that said Letters Patent is hereby corrected as shown below:

Column 1, line 33, delete "re" and insert --are--.

Column 5, line 56, delete "time stamp" and insert --timestamp--.

Signed and Sealed this

Sixteenth Day of August, 1994

*Attest:*

BRUCE LEHMAN

*Attesting Officer*      Commissioner of Patents and Trademarks